(12) United States Patent
Oberlaender et al.

(10) Patent No.: US 8,702,601 B2
(45) Date of Patent: Apr. 22, 2014

(54) MEDICAL ACCESS DEVICE HAVING A PROTECTION AGAINST AN EXCESSIVE APPLICATION OF LEVERAGE

(75) Inventors: Martin Oberlaender, Engen (DE); Michael Sauer, Tuttlingen (DE); Vincent Beysang, Guemar (FR)

(73) Assignee: Karl Storz GmbH & Co. KG (DE)

( * ) Notice: Subject to any disclaimer, the term of this patent is extended or adjusted under 35 U.S.C. 154(b) by 85 days.

(21) Appl. No.: 13/410,695

(22) Filed: Mar. 2, 2012

(65) Prior Publication Data
US 2012/0310049 A1 Dec. 6, 2012

(30) Foreign Application Priority Data
Jun. 6, 2011 (DE) .......................... 10 2011 103 526

(51) Int. Cl.
*A61B 1/32* (2006.01)
(52) U.S. Cl.
USPC ........................................................ 600/219
(58) Field of Classification Search
USPC ......... 600/210, 201, 208, 219, 220, 225, 218, 600/184, 190, 197; 606/105
See application file for complete search history.

(56) References Cited

U.S. PATENT DOCUMENTS

| | | | |
|---|---|---|---|
| 4,432,351 A * | 2/1984 | Hoary | 600/220 |
| 7,566,302 B2 * | 7/2009 | Schwer | 600/219 |
| 8,303,499 B2 * | 11/2012 | Hamada | 600/233 |
| 8,403,840 B2 * | 3/2013 | Wagner et al. | 600/210 |
| 8,484,924 B2 * | 7/2013 | Braun | 52/588.1 |
| 2008/0249371 A1 * | 10/2008 | Beckman et al. | 600/204 |

FOREIGN PATENT DOCUMENTS

| | | |
|---|---|---|
| DE | 2801696 A1 | 7/1979 |
| DE | 7801125 U1 | 3/1987 |
| DE | 69327786 T2 | 7/2000 |
| DE | 102009014524 A1 | 9/2010 |
| EP | 0043218 B1 | 1/1982 |
| EP | 2228024 A1 | 9/2010 |

* cited by examiner

*Primary Examiner* — Pedro Philogene
(74) *Attorney, Agent, or Firm* — St. Onge Steward Johnston & Reens LLC

(57) ABSTRACT

A medical access device for creating an access to a body for minimally invasive intervention has a hollow body assembled from at least two parts having longitudinal extending edges. Each part has a distal body portion and at an angle to the latter a proximal body portion. A locking mechanism locks the assembled proximal hollow body portions. The locking mechanism has a hook projecting from an edge of a proximal body. A nose of the hook can enter from proximal to distal in a recess in an edge joining said edge having said hook.

9 Claims, 4 Drawing Sheets

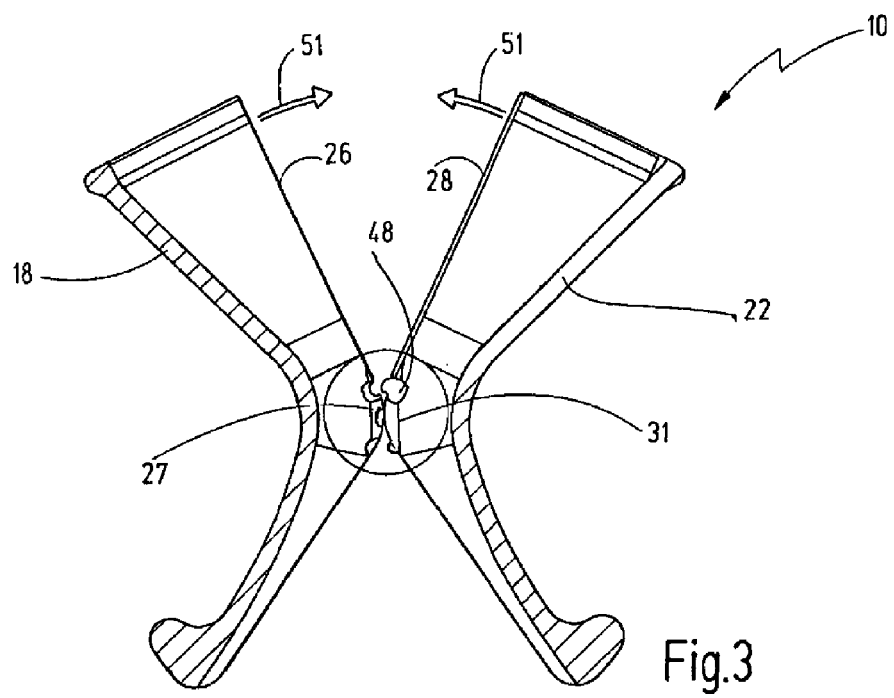
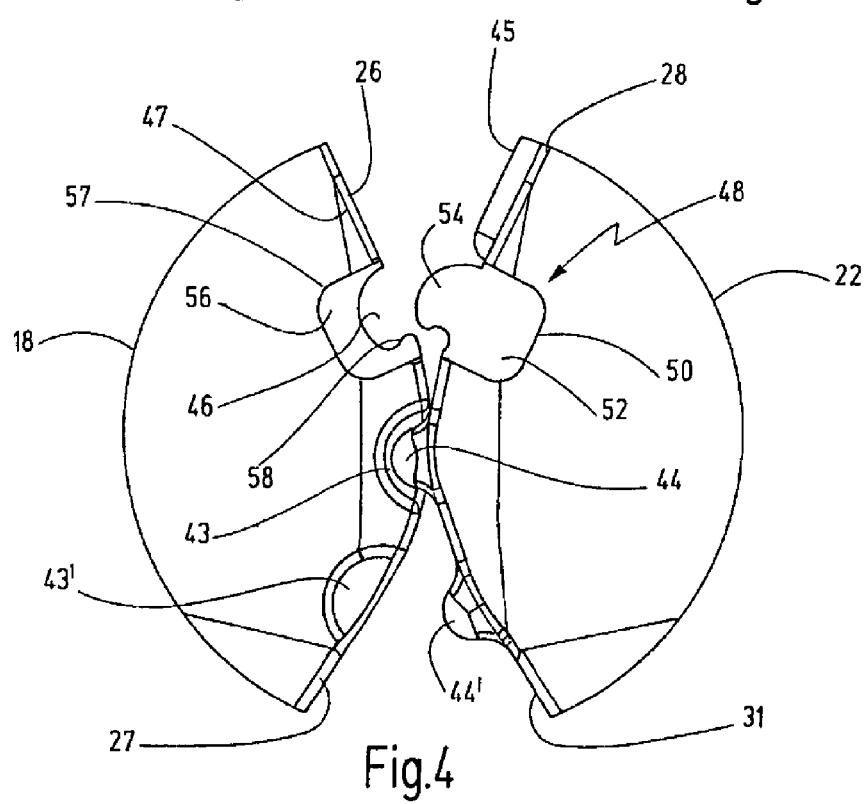

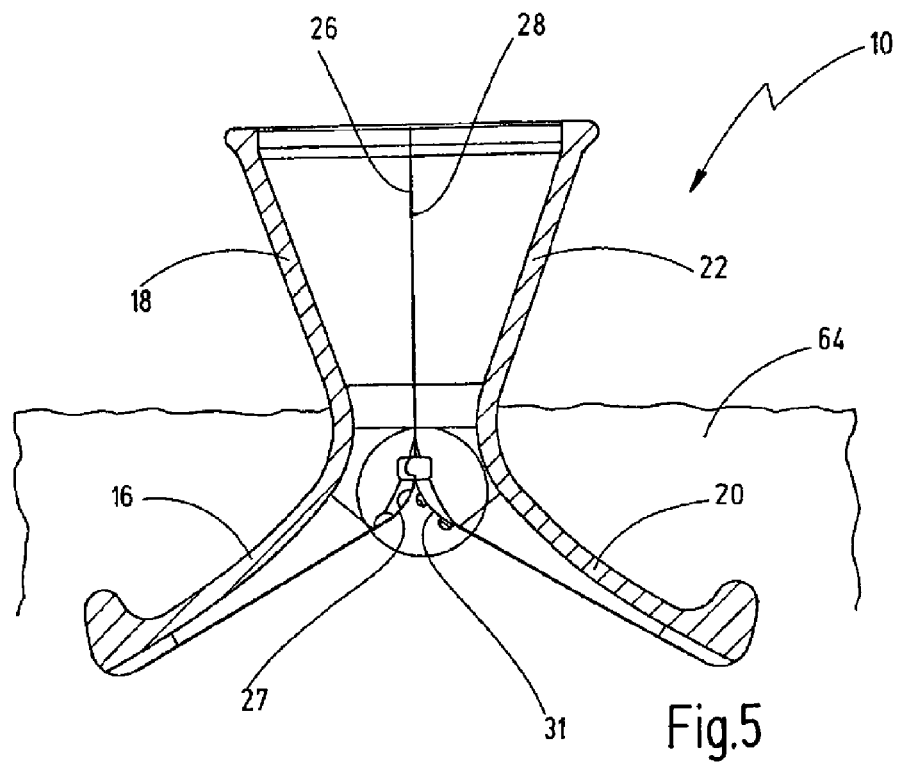
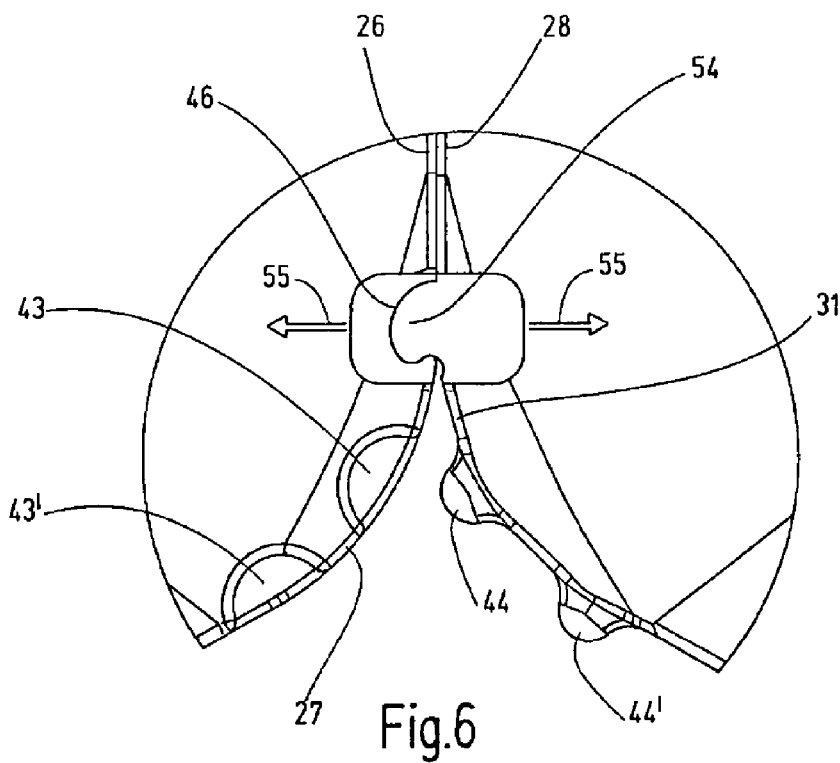

MEDICAL ACCESS DEVICE HAVING A PROTECTION AGAINST AN EXCESSIVE APPLICATION OF LEVERAGE

BACKGROUND OF THE INVENTION

The invention relates to a medical access device for creating an access for a minimally invasive intervention, with a hollow body assembled from at least two parts along the longitudinal edges thereof, wherein each part has a distal body portion and, at an angle to the latter, a proximal body portion, and wherein projections present on the longitudinal edges engage with recesses on an opposite longitudinal edge.

A medical device of this kind is known from EP 2 228 024 A1.

In a first position, the at least two parts are assembled such that the respective distal body portions form an approximately rod-shaped distal body. In this position, the medical device can be placed, for example, on an incision in the skin of an abdominal wall and can be driven through the abdominal wall into the abdominal cavity. In this state of assembly, the medical device thus functions as a trocar sleeve of a trocar, which is used for a laparoscopic intervention.

The proximal body portions, which are each angled laterally in relation to the respective distal body portions, extend to the sides from this assembled distal body and project above the skin or the abdominal wall. These proximal body portions are then pivoted such that they join together to form a proximal hollow body. In this process, the proximal body portions present in the abdominal space are pivoted laterally away from each other. A sealing cap is then fitted onto the proximal hollow body.

In this pivoting movement, the mutually opposite longitudinal edges of the bodies roll along each other in the curved transition area between the respective distal body portion and the respective proximal body portion. This rolling movement is guided by projections present on the longitudinal edges, which projections can engage in corresponding recesses on an opposite longitudinal edge.

These projections can be knobs or tongues that engage in corresponding depressions or grooves in the opposite longitudinal edges.

This arrangement of knobs or groove and tongues not only guides this rolling movement but also prevents the two parts from separating from each other transversely with respect to the surface of the longitudinal edges.

At the same time, the intensive interlocking of these toothing features ensures a relatively gas-tight seal along the longitudinal edges of the joined-together proximal body portions. In this way, it is possible, as is customary in laparoscopic surgery, to introduce an insufflation gas into the abdominal space through the proximal hollow body, which is formed by the two proximal body portions and is sealed off proximally by the cap, in order to inflate the abdominal space.

A particular advantage of the device is that a surgical instrument pushed through the latter can be tilted to and fro within a very large angle range. For the operating surgeon, this opens up a wide operating field for the surgical instruments that are pushed through the device, e.g. endoscopes, scissors, forceps and the like, for performing a surgical intervention.

In practice, it has been found that, when surgical instruments are extremely tilted and correspondingly oriented, they can have a tendency to move the two joined-together proximal body portions slightly away from each other as a result of the leverage exerted by the tilted instrument. This leverage acts in a proximal end area of one proximal body portion at the one side and in a distal end area of the adjacent proximal body portion at the other side. It has been observed that considerable gas losses occur as a result of gas escapes via the longitudinal edges of the joined-together proximal body portions, even when these are moved away from one another only by fractions of millimeters.

A vaginal speculum is known from German Utility Model G 78 01 125.3 and is composed of two shell-shaped parts, wherein each part has a distal body portion and, at an angle thereto, a proximal body portion.

In the area of the curvature, that is to say of the transition from the respective distal body portion to the proximal body portion, the two shell-shaped parts are firmly connected to each other by a joint. When the distal body portions are placed against each other, the speculum can be inserted into the vagina. When the proximal body portions are joined together to form a hollow body, the already inserted distal body portions then spread the vagina open. The physician can then make suitable visual observations through the vaginal speculum designed as a hollow body.

A locking device is provided to ensure that, during the observation, the two proximal body portions do not spread apart from each other again as a result of the restoring force of the vaginal tissue.

On one of the two proximal bodies, the locking device has tabs which protrude in a circumferential direction away from the longitudinal edges thereof. The tabs, in a cross section perpendicular to the longitudinal edges, widen in a wedge shape starting from the free end. The tip of the wedge extends in a radial direction in view of the longitudinal axis of the speculum. On the opposite proximal body portion, recesses are provided on the inner or the outer face of the wall, into which recesses the tabs fit and the wedge shape ensure a locking engagement.

For this purpose, however, the geometry and shape of the tabs must be such that they have a degree of elasticity allowing them to bend radially, in order to be able to be driven into the recesses on the inner or outer face of the wall surface of the other proximal body portion.

To release the locking mechanism, the operator has to exert a strong radially inward pressure so as to slightly deform the hollow body composed of the two locked proximal body portions, to an extend that a wedge-shaped tab can escape from the recess on the wall. In the case of a vaginal speculum, which is substantially larger than the device of the present application and which has a considerable wall thickness and is in most cases made of metals, an elastic tab construction of this kind and recesses on the wall of the other proximal body portion can be provided.

In the case of substantially smaller hollow bodies with thinner walls, like the device of the present application, such a construction will not be able to work in a reliable manner. There would be the danger of extremely tilted instruments causing deformations that allow the wedge-shaped tab to escape from the recess on the inner wall.

It is therefore an object of the present invention to provide a medical access device having a locking mechanism which prevents a release of the locking by tilted instruments inserted in the medical access device.

SUMMARY OF THE INVENTION

According to the invention, the object is achieved by a medical access device for creating an access to a body for a minimally invasive intervention, comprising a hollow body, assembled from at least two parts having longitudinally extending edges, said at least two parts being assembled along its respective longitudinally extending edges, each part having a distal body portion and, at an angle to the latter, a proximal portion, said distal body portions, when assembled along its edges, result in a distal body with laterally outwardly standing proximal body portions, and when moving said laterally outwardly standing proximal body portions inwardly together along said edges and along a curved transition area, a proximal hollow body results with laterally outwardly standing distal body portions, a sealing cap fitted onto a proximal end of said proximal hollow body and a locking mechanism locking said assembled proximal hollow body portions, wherein said locking mechanism having at least one hook projecting from an edge of a proximal body portion, said hook having a nose extending from proximal to distal, and having a recess in an edge joining said edge having said hook, said recess being cut into said edge opposite to said hook and said recess opens to said hook, a shape of said recess is in that, when moving said proximal body portions inwardly together by rolling said edges to be joined in a first direction along said curved transition area, said nose of said hook enters said recess from proximal to distal without a relative movement between hook and proximal part having said hook, and said recess blocks a movement of said hook out of said recess in a direction perpendicular to surfaces of said edges, thereby blocking a pulling away of joined edges, and wherein said nose moves out of said recess, without a relative movement between said hook and said proximal part having said hook, when moving said joined proximal parts by rolling it in a second direction counter to said first direction along said curved transition area.

The construction can be imagined as a kind of zip fastener in which, during the zip movement, the locking elements enter the corresponding recesses without necessarily requiring deformations of the material. In the movement in the opposite direction, these locking elements then escape again from the recesses. In other words, in the same way as one closes a zip fastener in one direction and opens it in the opposite direction.

During the rolling movement in the first direction, the approaching longitudinal edges of the proximal body portions move towards each other. The roll axes lie in the area of the curved transition area between distal body portion and proximal body portion.

By providing a hook having a nose that extends from proximal to distal, this nose can be driven from "above", i.e. from proximal to distal, into a corresponding recess on the opposite edge, without material deformations being necessary for this. The same also occurs in the opposite rolling movement, that is to say when the access instrument is to be removed again from the body, for which purpose the proximal body portions are spread apart from each other again.

In the case of small structural parts, and also in the case of structural parts made of plastic, the engagement of such a hook in a recess can provide a sufficient resistance force with respect to leverages acting on the two proximal body portions counter to the direction in which they were joined together. This prevents a pulling away of the edges joined together.

Thus, by means of simple and operationally reliable design features, it is possible to withstand leverages and to avoid a loss of gas, even in the case of very small structural parts.

It is possible to provide only one such hook. Alternatively, several such hooks can be distributed along the longitudinal edges of the proximal body portion.

A hook has the advantage of being an assembly aid when joining the parts together. The hook differs from other projections, for example knobs, and thus provides a clear orientation and therefore helps how one part is to be placed onto the other part and joined to the latter. This avoids an incorrect placement of the partial bodies in the sense of an axial offset along the longitudinal edges.

The principal holding together of the two parts is achieved by the cap fitted onto the proximal end of the joined-together proximal body portions.

But, leverages forces tend to move away joined edges of the proximal bodies the more these forces act away from the proximal end with the cap fitted thereon.

In practical application, that is to say when surgical instruments within the device are extremely tilted, the hook of the present invention avoid the joined-together proximal bodies from being moved away from another, particularly at areas rather away from the proximal end, and thus to avoid the associated escape of gas.

In another embodiment of the invention, the hook is designed as a nose which projects from the longitudinal edge of a proximal body portion and which nose can be driven in and out of a recess in the opposite longitudinal edge of the proximal body that is to be joined.

This measure has the advantage that the nose can be designed as a relatively stable rounded body, which enters or leaves the recess in a correspondingly smooth manner during the rolling movements. Even when using relatively small structural parts, this nose can be made so stable that it can also resist considerable leverages.

In another embodiment of the invention, the recess has an undercut, behind which the nose can be moved.

This measure has the advantage that withdrawal of the hook can be blocked by particularly simple structural means, namely by an undercut.

In another embodiment of the invention, the nose is configured in such a way that, when it has entered the recess, it lies flush in the recess.

This measure has several advantages. A flush contact between nose and recess permits a relatively large bearing surface across which the leverages can be distributed. At the same time, this has the advantage that, as a result of the flush contact, a particularly gas-tight connection to the outside is present in the area of the hook itself.

In another embodiment of the invention, the hook is designed as a projection on the longitudinal edge of one proximal body portion, with at least the wall thickness of the latter.

This measure has the advantage that the hook can be produced in a particularly simple way from the point of view of manufacturing technology. In the case of an injection-moulded part, the hook can be produced as an integral component part of the wall of the distal hollow body. Since this hook then projects from the longitudinal edge, it can have at least the width of the wall thickness, or, if appropriate, it can also be wider, such that a particularly resistant construction is ensured that takes up considerable leverages.

In another embodiment of the invention, the recess is designed as a material cutout through the entire wall thickness of the longitudinal edge of a proximal body portion.

This measure in turn also has several advantages. Such a recess can be produced very easily from the point of view of manufacturing technology. In the case of an injection-moulded part it can be provided, already during the original injection of the part. In the case of a body made from metal, this recess can be easily milled out. Here too, it is expedient to provide the recess through the entire material thickness, such that intimate contact is then possible with a correspondingly shaped hook.

In another embodiment, the hook is designed as an insertable part.

This measure has the advantage that the hook can initially be produced as a separate structural part and can then be inserted and embedded into the proximal body portion. This opens up the possibility, for example, of this hook being made from materials other than the material of the proximal body portion, in particular from more stable materials. Thus, for example, the hook can be designed as a metal part that can then be embedded into a body made of plastic, for example integrated with the latter during the injection of the plastic part.

In another embodiment of the invention, the recess is formed in an insertable part that can be inserted into the wall of a proximal body portion.

This affords in principle the same advantage, that is to say that the recess can be milled from a metal insert piece, and the latter can then be embedded into a proximal body portion that has been otherwise produced in advance. For example, this can also be done once again during the plastic injection moulding of a plastic part.

If the body is made of metal, the recess can be easily produced by removing material by milling.

In the case of the body being made of metal, so much material would have to be removed from the solid material that the hook is shaped protruding from the wall. This can be complicated and difficult.

Therefore, for example, the hook could be punched out as a prefabricated punched part and then inserted into a corresponding recess in the wall of the proximal body portion.

By virtue of the zip fastener principle, the hook can travel in and out of the recess in a manner free from deformation.

It is thus possible, in the area of the hook, to avoid material fatigue.

In another embodiment of the invention, at least one hook is arranged in the area of a curvature in a transition area between the longitudinal edges of a proximal body portion and the corresponding distal body portion.

If it is arranged in the curved transition area between a distal body portion and a proximal body portion, a hook provides an optimum resistance force to the leverages that could cause an opening of the joined edges. This is because, as is shown in the drawings, a tilted instrument engages precisely in this curved area in order to exert these leverages. The tilted instrument engages on the one hand on the proximal end and on the other hand in the curved transition area of a part. The lever action is thus resisted by the hook precisely at the location where the leverages are applied directly.

It will be appreciated that the aforementioned features and the features still to be explained below can be used not only in the cited combinations but also in other combinations or singly, without departing from the scope of the present invention.

BRIEF DESCRIPTION OF THE DRAWINGS

The invention is described and explained in greater detail below on the basis of a selected illustrative embodiment and with reference to the attached drawings, in which:

FIG. 3 shows a longitudinal section through the two joined parts from FIG. 1, an intermediate state being depicted that corresponds to a change-over from the pivoting position of FIG. 1 to FIG. 2;

FIG. 4 shows a much enlarged depiction of the area outlined with a circle in FIG. 3, FIG. 5 shows a sectional view which corresponds to FIG. 3 and in which the proximal body portions, as can also be seen in FIG. 2, are joined together, FIG. 6 shows a greatly enlarged area of the area outlined with a circle in FIG. 5.

DESCRIPTION OF PREFERRED EMBODIMENTS

A medical device according to the invention shown in the figures is designated overall by reference number 10.

Figure 1:
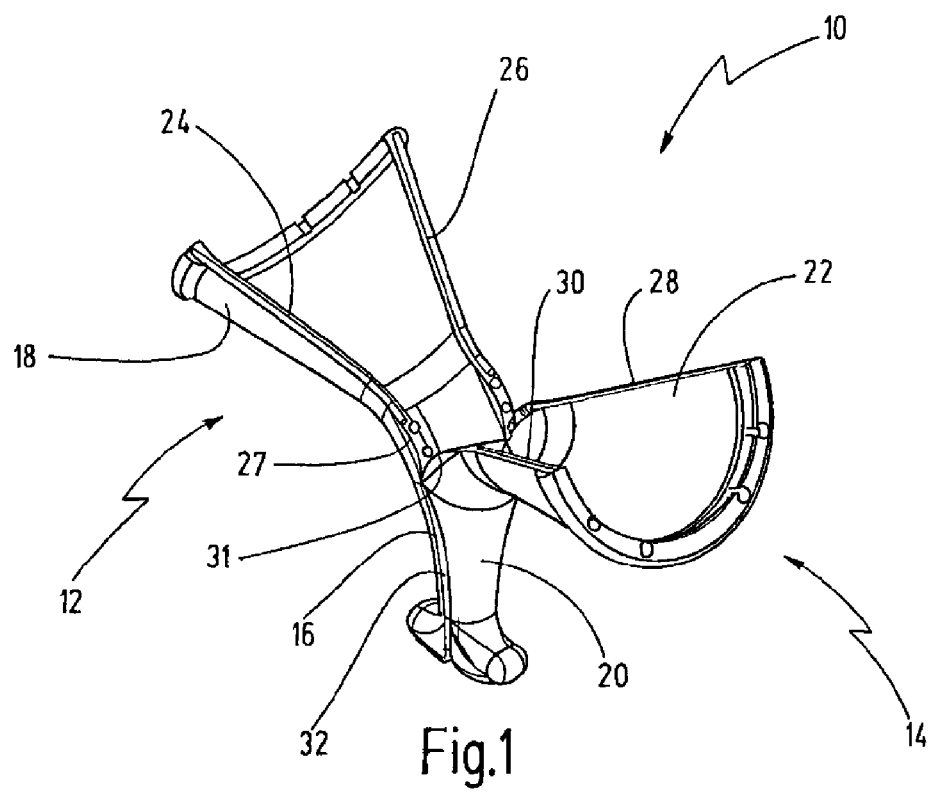
FIG. 1 shows two parts of a device according to the invention, which parts, in a first position for insertion of the instrument, are assembled via the distal body portions.

FIG. 1 shows that the medical device 10 has a first part 12 and a second part 14.

The first part 12 has a distal body portion 16, from which a proximal body portion 18 protrudes at an angle. In the area of the proximal body portion 18, the first part 12 is designed as a hollow body having a shell shape and widening in the proximal direction.

The second body 14 also has a distal body portion 20 and, protruding at an angle from the latter, a proximal body portion 22. This proximal body portion 22 is also in turn designed as a hollow body having a shell shape and widening in the proximal direction.

The size and the geometry of the two distal body portions 16 and 20 are such that, when they are joined together as shown in FIG. 1, they form a distal body 32, which is approximately rod-shaped.

It will also be seen from FIG. 1 that the proximal body portion 18 has two longitudinal edges 24 and 26 extending lengthwise. Seen from the proximal direction, these longitudinal edges 24 and 26 initially extend approximately rectilinearly and, in a curved transition area 27, merge into the corresponding rectilinear longitudinal edges of the distal body portion 16.

The proximal body portion 22 of the second part 14 likewise has two corresponding shaped longitudinal edges 28 and 30 which merge, via a curvature 31, into the corresponding longitudinal edges of the distal body portion 20. In the state of assembly shown in FIG. 1, the two joined-together distal body portions 16 and 20 are placed in a living body, for example at an incision in the abdominal wall and are driven through this incision into the interior of the abdomen, in a manner that is known per se and that is described in detail particularly in EP 2 228 024 A1 mentioned at the outset.

Thereafter, the proximal body portions 18 and 22, still spread apart from each other, extend above the surface of the skin.

Figure 2:
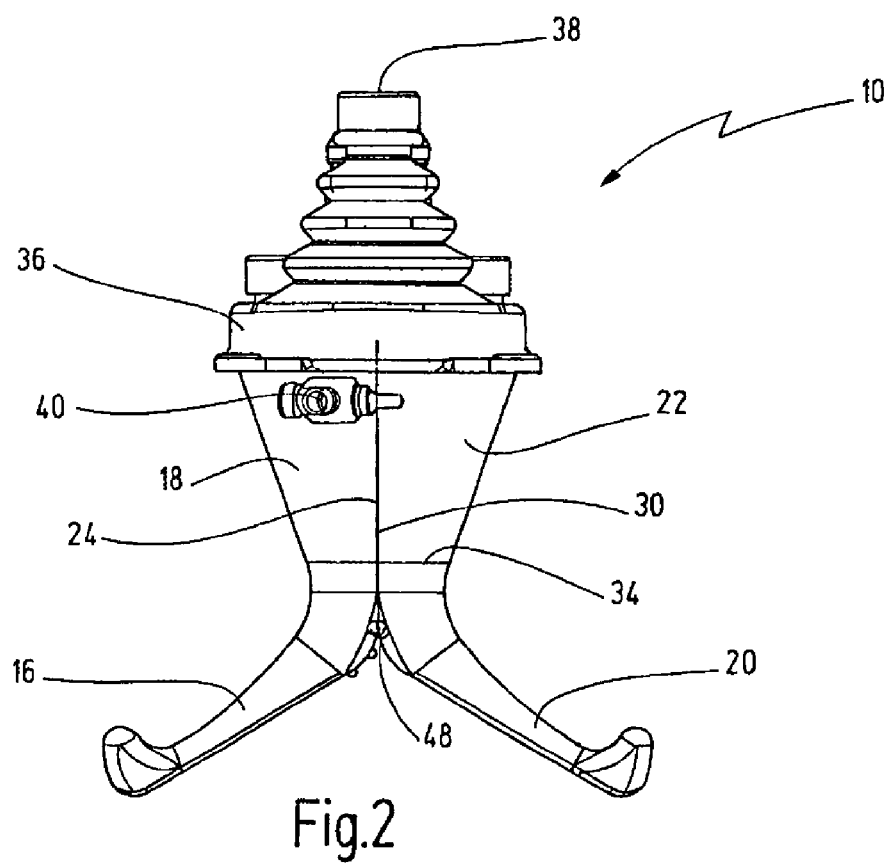
FIG. 2 shows a side view of the medical device from FIG. 1, after the latter has been introduced into a living body and the two proximal body portions have been joined together and a proximal closure cap has been fitted.

The two parts 12 and 14 lying on each other along its distal body portions 16 and 20 are now folded such that the two proximal body portions 18 and 22 are joined together to form a proximal hollow body 34, as is shown in FIG. 2.

During this movement, the two proximal body portions 18 and 22 roll over each other along their longitudinal edges 24, 26 and 28, 30 and over a curved transition area 27 and 31, respectively.

A sealing closure cap 36, which has several functions, is then fitted onto the proximal end of the joined-together proximal body portions 18 and 22, as can be seen from FIG. 2.

In the state of assembly shown in FIG. 2, the cap 36 holds the two body portions 18 and 22 together in the form of a proximal hollow body 34, since said cap is pushed over the proximal edge of the proximal body portions 18 and 22. At the same time, it ensures a gas-tight seal in the proximal direction. In the cap 36, there is at least one inlet 38 through which a surgical instrument can be pushed through the cap 36 and the distal hollow body 34 into the interior of the human or animal body, in a manner known per se.

Mounted on the outer face of the proximal body portion 18 is a gas attachment 40 via which a gas, in most cases $CO_2$, can be supplied for inflating the interior of the abdomen.

The cap 36 ensures a tight seal in the proximal direction.

Problem areas are sections of the joined longitudinal edges 24 and 30 of the proximal body portion that bear on each other, and also the corresponding edges 26 and 28 bearing on each other which sections are relatively far away from the cap 36. In order to ensure a seal that is as gas-tight as possible here, a row of toothing features is provided on the longitudinal edges 26 and 28, as can be seen in particular in FIGS. 3 and 4. It will be seen in particular from the enlarged view in FIG. 4 that knobs 44, 44' protrude from the longitudinal edge 28 and can be fitted into opposite depressions 43, 43', respectively, on the longitudinal edge 26.

In the more proximal area, a tongue 45 protrudes from the longitudinal edge 28 and can fit into a longitudinal groove 47 (not visible in detail here) on the opposite edge 26.

This structure not only leads to a targeted and guided rolling movement of the longitudinal edges 28 and 26 when the proximal body portions 18 and 20 are joined together but also at the same time provides toothing features which block a release of the two proximal body portions 18 and 22 transversely with respect to the longitudinal extent of the longitudinal edges.

It will be seen in particular from the enlarged view in FIG. 4 that, in the curved transition area 31 of the longitudinal edge 28 of the proximal body portion 22, a hook 48 protrudes from the latter and can be fitted into a corresponding recess 46 on the opposite longitudinal edge 26 of the proximal body portion 18 when the longitudinal edges 26 and 28 are moved towards each other in a first direction, as is indicated by the two arrows 51 in FIG. 3, when they are being joined together. The hook 48 has a nose 54, which extends sloping in the distal direction.

The recess 46 has a corresponding undercut 58. During the rolling movement and joining together, the nose 54 of the hook 48 now runs from distal to proximal into the recess 46 and behind the undercut 58, as can be seen from the change from FIG. 4 to FIG. 6.

No material deformation is necessary for this. Rather, during the rolling movement along the curved transition area 31 or the curved transition area 27, the nose 54 of the hook 48 runs snugly into the recess 46 and behind the undercut 58.

For removing the device 10 after a surgical action, the cap 36 is removed and the proximal body portions 18 and 22 are spread away from one another with a rolling movement along its edges in a second direction counter to the first direction. The distal body portions 16 and 20 join, as shown in FIG. 1, and the device can be removed from the living body.

The hook/recess construction provides a locking mechanism locking the assembled proximal hollow body portions against excessive application of leverage.

In the state shown in FIG. 2 and in FIGS. 5 and 6, the hook 48 thus blocks a movement of the two joined-together proximal body portions 18 and 22 counter to the direction of joining together, as indicated by arrows 55 in FIG. 6. This blocks a pulling away of the joined edges 24 and 30 as well as edges 26 and 28 along a direction of arrows 55 which is perpendicular to the surface of the edges.

Figure 7:
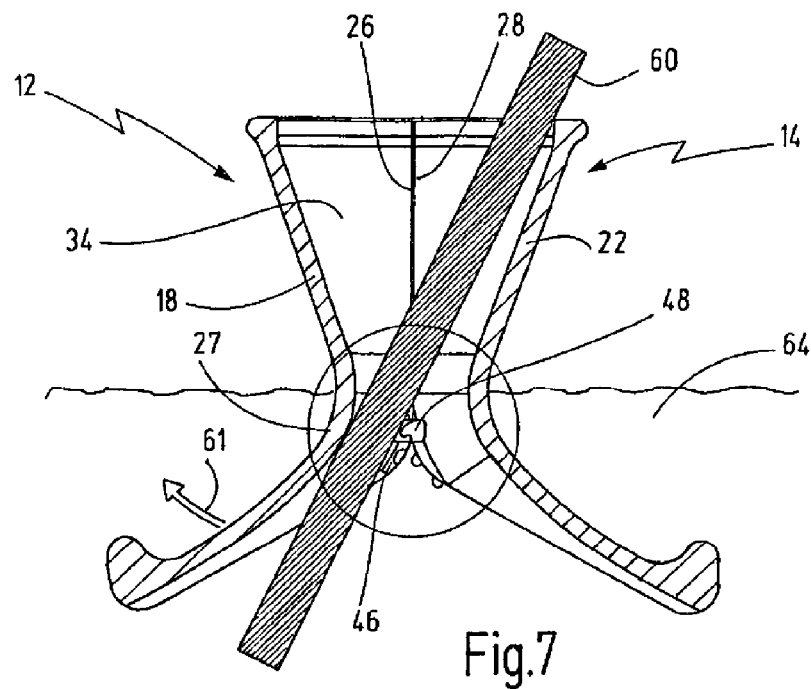
FIG. 7 shows, in a cross section corresponding to the view in FIG. 5, the insertion of a rod-shaped instrument that is extremely tilted and that tends to move away the two joined parts.
Figure 8:
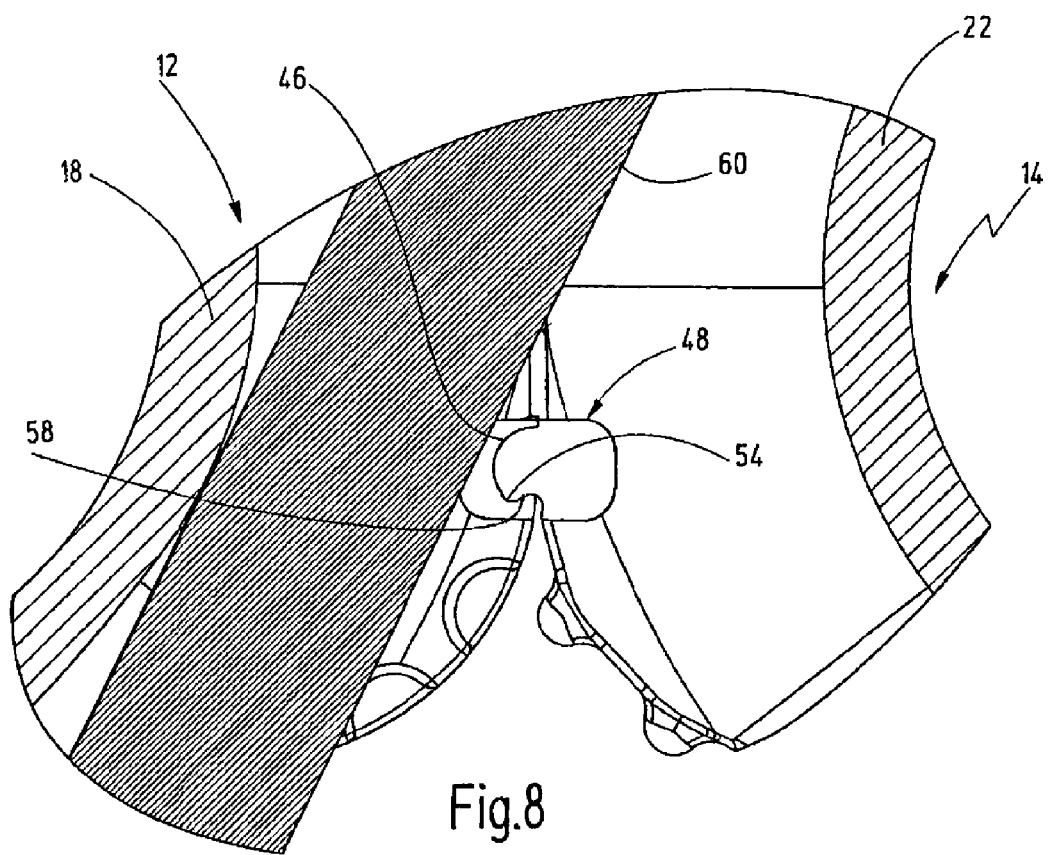
FIG. 8 shows a greatly enlarged view of the area outlined with a circle in FIG. 7.

FIGS. 7 and 8 show a situation in which leverages occur that are of such a kind that they tend to move the joined-together longitudinal edges 26 and 28 slightly away from each other also when the cap 36 is fitted.

FIG. 7 shows that a rod-shaped instrument 60 is inserted in and through the device and that the instrument 60 is extremely tilted.

It thus abuts, at the proximal end, against the inner upper proximal edge, for example of the proximal body portion 22.

This strongly tilted instrument 60 strikes the distal end region of the proximal body portion 18 of the body part 12 and tends to lever it open, particularly in the area of the curvature 27, i.e. move it away from the longitudinal edge 28.

If such a leverage is not applied, the restoring force of the abdominal wall 64 through which the instrument 10 according to the invention is pushed into a living body is normally sufficient to ensure an adequate pressing force of the two parts 12 and 14 in this area in order to avoid gas losses.

However, if an instrument 60 is tilted as strongly as is indicated in FIG. 7, there is the danger of the two parts 12 and 14 being moved apart.

It will be seen from the enlarged view in FIG. 8 that the nose 54 of the hook 48, which has been moved behind the undercut 58, blocks this movement along arrows 55 as shown in FIG. 6. This works particularly if it is arranged at this location of the curved transition area.

Of course, this structure also provides a blocking effect if the instrument 60 is tilted in the opposite direction.

Only one such hook is shown in the illustrative embodiment, but it is also possible for several such hooks to be provided in the area of the curvature in the direction of the proximal end if it is feared that extremely strong leverages can be exerted because of the inserted instruments.

It is indicated in FIG. 4 that the hook 48 can be designed as a separate part 50 that is fitted or embedded into the wall of the proximal body portion 22 in the area of the longitudinal edge 28. For this purpose, the hook has a cornered insert piece 52 that is inserted with a firm fit into a corresponding recess or milling. This can be done by screwing or soldering, or also by injection in a plastic injection moulding operation.

Correspondingly, a part 56 that has the recess 46 is fitted or embedded on the opposite longitudinal edge 26. This part is then inserted or anchored correspondingly.

This opens up the possibility, for example, of producing the parts 12 and 14 from an inexpensive plastic material in a single injection moulding operation. To effectively withstand excessive leverages and to take up considerable forces, the parts 50 and 56 can then be produced from more resistant material, e.g. metal, and used as insert pieces. This can already take place, for example, in the original injection moulding operation.

In this way, a single hook of this kind can already be sufficient to prevent a moving away of joined edges due to leverages.

It is of course also possible for the hook and recess, produced as parts made from plastic, to be produced directly in the injection moulding operation.

In the case of instruments made of metal, the recess can be made by a simple milling operation, but the hook would then have to be shaped from the solid material or correspondingly fitted. In this respect, a person skilled in the art has many possible options available for providing structures according to client requirements.

It can be seen in particular from FIG. 8 that the hook 48, or the nose 54 thereof, corresponds exactly to the contour of the recess 46 and is thus received flush inside the latter.

This additionally contributes to a gas-tight seal in this area, specifically against passage of gas transverse to the longitudinal direction of the longitudinal edges 26, 28 and 24, 30 in the area of the hook 48.

What is claimed is:

1. A medical access device for creating an access to a body for a minimally invasive intervention, comprising
    a hollow body, assembled from at least two parts having longitudinally extending edges,
    said at least two parts being assembled along its respective longitudinally extending edges,
    each part having a distal body portion and, at an angle to the latter, a proximal portion,
    said distal body portions, when assembled along its edges, result in a distal body with laterally outwardly standing proximal body portions, and when moving said laterally outwardly standing proximal body portions inwardly together along said edges along a curved transition area, a proximal hollow body results with laterally outwardly standing distal body portions,
    a sealing cap fitted onto a proximal end of said proximal hollow body, and
    a locking mechanism locking said assembled proximal hollow body portions, wherein
    said locking mechanism having at least one hook projecting from an edge of a proximal body portion, said hook having a nose extending from proximal to distal, and having a recess in an edge joining said edge having said hook, said recess being cut into said edge opposite to said hook and said recess opens to said hook,
    a shape of said recess is in that, when moving said proximal parts inwardly together by rolling said edges to be joined in a first direction along said curved transition area, said nose of said hook enters said recess from proximal to distal without a relative movement between hook and proximal part having said hook, and said recess blocks a movement of said hook out of said recess in a direction perpendicular to surfaces of said edges, thereby blocking a pulling away of joined edges, and wherein said nose moves out of said recess, without a relative movement between said hook and said proximal part having said hook, when moving said joined proximal parts by rolling it in a second direction counter to said first direction along said curved transition area.

2. The medical device of claim 1, wherein said hook having said nose projects from a longitudinal edge of a proximal body portion, which nose can be moved in and out of a recess in an opposite longitudinal edge of a proximal body to be joined.

3. The medical device of claim 1, wherein said recess has an undercut behind which said nose of said hook can be moved.

4. The medical device of claim 1, wherein said nose is shaped in such a way, when it has moved into said recess, it lies flush in said recess.

5. The medical device of claim 1, wherein said hook is designed as a projection on a longitudinal edge of a proximal body portion, a thickness of said hook corresponds at least to a wall thickness of said proximal body portion.

6. The medical device of claim 1, wherein said recess is designed as a material cutout through an entire wall thickness of said longitudinal edge of said proximal body portion to be joined with said body portion having said hook.

7. The medical device of claim 1, wherein said hook is designed as a separate part which is embedded into said proximal body portion.

8. The medical device of claim 1, wherein said recess being formed in a separate part that is embedded into a wall of said proximal body portion.

9. The medical device of claim 1, wherein said at least one hook is arranged in said curved transition area.

\* \* \* \* \*